United States Patent [19]
Billings et al.

[11] 3,989,845
[45] *Nov. 2, 1976

[54] ANESTHETIC CHLOROCYCLOPROPANES
[75] Inventors: Charles Alden Billings, Concord; Gerald Joseph O'Neill, Arlington; Charles William Simons, Bedford; Robert S. Holdsworth, Arlington, all of Mass.
[73] Assignee: W. R. Grace & Co., Cambridge, Mass.
[ * ] Notice: The portion of the term of this patent subsequent to Feb. 11, 1992, has been disclaimed.
[22] Filed: Dec. 26, 1974
[21] Appl. No.: 536,589

[52] U.S. Cl. .............................................. 424/352
[51] Int. Cl.² ..................................... H61K 31/025
[58] Field of Search ...................................... 424/352

[56] References Cited
UNITED STATES PATENTS
3,825,606   7/1974   O'Neill et al. ...................... 424/352
3,839,589   10/1974  O'Neill et al. ...................... 424/352
3,865,950   2/1975   O'Neill et al. ...................... 424/352

Primary Examiner—Jerome D. Goldberg
Attorney, Agent, or Firm—Armand McMillan; C. E. Parker

[57] ABSTRACT

The following chlorocyclopropanes have been found to possess utility as general inhalation anesthetics: 1,1-dichloro-2-methyl-2,3,3-trifluorocyclopropane, 1,2-dichloro-1-fluoro-2-methylcyclopropane, 1,1,2-trichloro-2,3,3-trifluorocyclopropane, 1,1-dichloro-2-trifluoromethyl-2,3,3-trifluorocyclopropane, 1,2-dichloro-1,2,3,3-tetrafluorocyclopropane, 1,1,2,2-tetrachloro-3,3-difluorocyclopropane and 1,1-dichloro-2,3,3-trifluorocyclopropane.

8 Claims, No Drawings

ANESTHETIC CHLOROCYCLOPROPANES

THE PRIOR ART

In the continuing search for general inhalation anesthetics, there has been recently discovered a few halocyclopropanes and methylhalocyclopropanes and some methyl halocycloproyl ethers. These compounds are disclosed in U.S. Pat. Nos. 3,865,950, 3,839,589 and 3,769,429 as well as in pending applications Ser. No. 499,761 (filed Aug. 22, 1974) for the methylcyclopropanes, and Ser. No. 451,677 (filed Mar. 15, 1974) for the methyl ethers. Prior to these current developments, which have been contributed to the art by the present applicants, the only known cyclopropane compounds with a claim to anesthetic utility were cyclopropane itself and the 1-methyl-1-trifluoromethylcyclopropane reported by Krantz and Rudo [Handbuch of Experimental Pharmakologie 20 (1), at page 525 (1966)]. On assessing the progress reported in the art, as just reviewed, one must agree with these authors who, after an extensive compilation of the results of a few hundred tests on fluorinated compounds, conclude that cyclic halogenated compounds tend to be toxic. In fact, it has been the applicants' experience generally that for each useful compound discovered, there has been found one or more other structurally closely related compounds which are either useless or deleterious.

In the case of chlorinated cycloalkanes specifically, the only compound mentioned in the literature in an anesthetic context is the 1,2-dichlorohexafluorocyclobutane, a compound which is said to be toxic, in contrast to its 1,2-dihydro-analog to which anesthetic properties have been ascribed [Burns et al, Anaesthesia 16 No. 1, page 14 (January 1961)].

Thus, despite the disclosures in recent years, it can be reasonably said that little has been added to the understanding of the mode of action of chemical compounds in this physiological role and, because of this, the relationship of the similarities and differences between fairly similar compounds with either their toxic or therapeutic properties remains substantially unidentified. The discovery of additional substances possessing a desirable combination of properties for anesthetic purposes still lies, therefore, beyond the scope of routine expertise.

SUMMARY OF THE INVENTION

Several dichlorocyclopropane compounds have now been found to possess useful anesthetic activity. This is rather surprising in view of the toxicity of the only dichlorocycloalkane reported upon before the contributions of the present inventors and also, in the case of many of the compounds of the present invention, the absence of the ring hydrogen which is believed to be necessary for anesthetic action. The compounds which form the basis of this invention are the following ones: 1,1-dichloro-2-methyl-2,3,3-trifluorocyclopropane, 1,2-dichloro-1-fluoro-2-methylcyclopropane, 1,1,2-trichloro-2,3,3-trifluorocyclopropane, 1,1-dichloro-2-trifluoromethyl-2,3,3-trifluorocyclopropane, 1,2dichloro1,2,3,3-tetrafluorocyclopropane, 1,1,2,2-tetrachloro-3,3-difluorocyclopropane and 1,1-dichloro-2,3,3-trifluorocyclopropane.

DETAILED DESCRIPTION

The chlorocyclopropanes of this invention may be synthesized by any several methods depending on the availability of starting materials and on the yield considered acceptable under the circumstances. The methods actually used in the preparation of the instant compounds are illustrated in the following examples.

EXAMPLES 1 to 5

Several of the compounds studied were synthesized by the thermal decomposition of trichloromethyltrifluorosilane in the presence of an appropriate olefin, according to a method disclosed in J. Chemical Soc., Perkin I, 1071-8 (1973). The trichloromethyltrifluorosilane in turn was prepared by chlorination of methyltrichlorosilane [Chem. Ber. 87, 282–7 (1954)] followed by fluorination of the trichloromethyltrichlorosilane by antimony trifluoride [Ber. 97 (6), 1673–6 (1964)].

Specifically, the cyclization was carried out in a clean, dry stainless steel autoclave. The autoclave was first evacuated and cooled in a dry iceacetone bath. The trichloromethyltrifluorosilane and the olefin were introduced and the mixture was heated at 140°–5° C for 20 to 24 hours. The vacuum distillate obtained from the autoclave was washed with aqueous base.

The quantities and types of materials used and the product and yield obtained are summarized in Table 1.

TABLE 1

| | Synthesis of Certain Chlorocyclopropanes | | | | |
|---|---|---|---|---|---|
| | TreClmethyl-triFsilane | Olefin | Cyclopropane Product Yield* | | |
| Ex. | (mole) | (mole) | (Boiling Point) (° C) | (Density) ($d_4^{20}$) | (Refr Index) ($n_D^{20}$) |
| 1 | 0.42 | 1,1,2-triF-prop-1-ene 0.46 | 1,1-diCl-2-$CH_3$-triF- 86.5° C | 1.434 | 64% 1.3860 |
| 2 | 0.35 | Cl-triF-ethylene 1.25 | 1,1,2-triCl-triF- 80.5° C | 1.620 | 86.6% 1.3984 |
| 3 | 0.55 | hexaF-propene 1.02 | 1,1-diCl-2-$CF_3$-triF- 58° C | 1.600 | 75% 1.3329 |
| 4 | 0.73 | triF-ethylene 1.7 | 1,1-diCl-2,3,3-triF- 63° C | 1.535 | 76% 1.3760 |
| 5 | 0.58 | 1,1-diCl-diF-ethylene 1.24 | 1,1,2,2-tetraCl-diF- 120° C | 1.682 | 78% 1.4469 |

*Based on silane

EXAMPLE 6

1,2-Dichlorotetrafluorocyclopropane was prepared in good yield by the reaction of hexafluoropropylene oxide with an excess of 1,2-dichlorofluoroethylene at 185° C for 6 to 8 hours in a stainless steel autoclave. The propylene oxide first decomposes to form the carbene :$CF_2$[J. Org. Chem 31, 2312 (1966)] which in turn cyclizes with the ethylene. The product obtained had a boiling point of 40° C, a density ($d_4^{20}$) of 1.593 and a refractive index ($n_D^{25}$) of 1.3419.

EXAMPLE 7

1,2-Dichloro-1-fluoro-2-methylcyclopropane was also prepared by the cyclization of a halocarbene with an olefin. The carbene, :CFCl, was prepared in concentrated sodium hydroxide solution from dichlorofluoromethane with the assistance of triethylbenzylammonium bromide [Synthesis 2, 112 (1973)].

A stainless steel autoclave was used to which were added 400 g of 50% aqueous sodium hydroxide and 2 g of triethylbenzylammonium bromide. The container was sealed, evacuated of air and cooled to −75° C. 2-Chloropropene, 1.2 moles, and dichlorofluoromethane, 1.55 moles, were introduced. After the autoclave had warmed to 0° to 20° C and the agitator had become free, stirring was carried out for 20 hours. The product was obtained by vacuum distillation and separation from the water in a funnel, in a yield of 42% based on the methane. The purified product had a boiling point of 100° C, a density ($d_4^{20}$) of 1.252 and a refractive index ($n_D^{25}$) of 1.4216.

EXAMPLES 8 to 14

The physiological effects of the cyclopropanes prepared in the preceding examples were demonstrated as follows, using a standard test for evaluation of inhalation anesthetics similar to that described in Robbins [J. Pharmacology and Experimental Therapeutic 86, 197 (1946)].

Mice were exposed to the anesthetic for a period of 10 minutes in a rotating drum. Observations were then made of the pinch reflex, the corneal reflex and the return of the righting reflex. At least four graded doses were employed to determine the minimum concentration required to anesthetize 50% of the mice used ($AC_{50}$) and the minimum concentration required to kill 50% of the mice ($LC_{50}$). The anesthetic index (AI) was then calculated from these minimum concentrations. The results of these tests are summarized in the following table.

the type commonly used for conventional anesthetics of comparable boiling point, e. g. halothane, and they may be used in admixture with pharmaceutically acceptable diluents and stabilizers such as thymol, or in combination with one or more of the known inhalation anesthetics, such as nitrous oxide, ether, halothane, chloroform, methoxyflurane and the like. In short, it should be understood that variations can be carried out in either the preparation or the administration of these compounds depending on factors such as economic considerations, level and duration of anesthesia desired, subject treated, and the like.

What is claimed is:

1. The process of inducing anesthesia in a mammal, which comprises administering by inhalation to said mammal an effective quantity for inducing anesthesia, of a cyclopropane selected from the group consisting of:
 1,1-dichloro-2-methyl-2,3,3-trifluorocyclopropane,
 1,2-dichloro-1-fluoro-2-methylcyclopropane,
 1,1,2-trichloro-2,3,3-trifluorocyclopropane, 1,1-dichloro-2-trifluoromethyl-2,3,3-trifluorocyclopropane, 1,2-dichloro-1,2,3,3-tetrafluorocyclopropane, 1,1,2,2-tetrachloro-3,3-difluorocyclopropane and 1,1-dichloro-2,3,3-trifluorocyclopropane.

2. The process of claim 1 wherein the cyclopropane employed is 1,1-dichloro-2-methyl-2,3,3-trifluorocyclopropane.

3. The process of claim 1 wherein the cyclopropane employed is 1,2-dichloro-1-fluoro-2-methylcyclopropane.

4. The process of claim 1 wherein the cyclopropane employed is 1,1,2-trichloro-2,3,3-trifluorocyclopropane.

5. The process of claim 1 wherein the cyclopropane employed is 1,1-dichloro-2-trifluoromethyl-2,3,3-trifluorocyclopropane.

6. The process of claim 1 wherein the cyclopropane employed is 1,2-dichloro-1,2,3,3-tetrafluorocyclopropane.

7. The process of claim 1 wherein the cyclopropane employed is 1,1,2,2-tetrachloro-3,3-difluorocyclopropane.

Table 2

ANESTHETIC PROPERTIES OF CHLOROCYCLOPROPANES

| Ex. | Cyclopropane | $AC_{50}$ (% volume) | $LC_{50}$ | AI ($LC_{50}/AC_{50}$) |
|---|---|---|---|---|
| 8 | 1,1-diCl-2-CH$_3$-triF- | < 1% | 4–6%* | 4–6 |
| 9 | 1,2-diCl-1-F-2-CH$_3$ | < 1% | 2–4% | >2 |
| 10 | 1,1,2-triCl-triF- | 1.5% | 2–10% | >3 |
| 11 | 1,1-diCl-2-CF$_3$-triF- | 4% | > 10% | ~2 |
| 12 | 1,2-diCl-tetraF- | 6–10% | < 20% | ~2 |
| 13 | 1,1,2,2-tetraCl-diF- | 0.25% | 1% | ~4 |
| 14 | 1,1-diCl-2,3,3-triF- | < 2% | 4–6% | 2–3 |

*Where two figures are given, the actual value lies between them.

The compounds of this invention are therefore capable of inducing a state of anesthesia in air-breathing mammals, from which the latter recover, provided that the lethal concentration of anesthetic vapors is not reached. The compounds can be stored in containers of pane.

8. The process of claim 1 wherein the cyclopropane employed is 1,1-dichloro-2,3,3-trifluorocyclopropane.

* * * * *